(12) United States Patent
Oguri

(10) Patent No.: US 8,441,362 B2
(45) Date of Patent: May 14, 2013

(54) MOISTURE DETECTION LABEL, MOISTURE DETECTION DEVICE, MOISTURE DETECTION METHOD, POWER SHUTOFF METHOD, AND ELECTRONICS DEVICE

(75) Inventor: Shinji Oguri, Saitama (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 13/443,432

(22) Filed: Apr. 10, 2012

(65) Prior Publication Data

US 2012/0218673 A1 Aug. 30, 2012

Related U.S. Application Data

(63) Continuation of application No. 11/203,244, filed on Aug. 15, 2005, now Pat. No. 8,242,919.

(30) Foreign Application Priority Data

Aug. 16, 2004 (JP) ................................. 2004-236541

(51) Int. Cl.
*G08B 21/00* (2006.01)
*G08B 21/20* (2006.01)

(52) U.S. Cl.
USPC ........... 340/605; 428/343; 428/209; 428/354; 428/349; 73/53.01; 73/40; 73/763; 73/865.9; 204/403.14; 252/502; 340/604; 340/679; 340/618

(58) Field of Classification Search ................. None
See application file for complete search history.

(56) References Cited

U.S. PATENT DOCUMENTS

| 4,297,686 | A |   | 10/1981 | Tom |   |
|---|---|---|---|---|---|
| 4,970,122 | A |   | 11/1990 | Palanisamy |   |
| 4,972,179 | A |   | 11/1990 | Akiba |   |
| 5,286,415 | A | * | 2/1994 | Buckley et al. | 252/502 |
| 6,175,310 | B1 | * | 1/2001 | Gott | 340/605 |

FOREIGN PATENT DOCUMENTS

| JP | 3-199954 A | 8/1991 |
|---|---|---|
| JP | 7-065948 B2 | 7/1995 |
| JP | 2574924 B2 | 10/1996 |
| JP | 2000-019136 A | 1/2000 |
| JP | 2000-162081 A | 6/2000 |
| JP | 2001-119459 A | 4/2001 |
| JP | 2002-082080 A | 3/2002 |
| JP | 2002-111838 A | 4/2002 |
| JP | 2003-59467 A | 2/2003 |
| JP | 2003-283619 A | 10/2003 |
| JP | 2004-120849 A | 4/2004 |

* cited by examiner

*Primary Examiner* — Sally Merkling
(74) *Attorney, Agent, or Firm* — Sughrue Mion, PLLC

(57) ABSTRACT

Provided is a moisture detection device including: a moisture detection label that has at least a pair of detection terminals and a pattern, the detection terminals being provided on a base material with an insulated front surface, the pattern being provided on the surface of the base material and formed between the detection terminals with water-dispersible and conductive paint; and detection circuit which detects an electrical connection state between the detection terminals.

30 Claims, 16 Drawing Sheets

| CONTROL TERMINAL | H | L |
|---|---|---|
| SWITCH | ON | OFF |

MOISTURE DETECTION LABEL, MOISTURE DETECTION DEVICE, MOISTURE DETECTION METHOD, POWER SHUTOFF METHOD, AND ELECTRONICS DEVICE

CROSS REFERENCE TO RELATED APPLICATIONS

This application is a continuation of U.S. patent application Ser. No. 11/203,244 filed Aug. 15, 2005, now U.S. Pat. No. 8,242,919, which claims priority to Japanese Patent Application No. 2004-236541, filed Aug. 16, 2004, the contents of all of which are incorporated herein by reference.

BACKGROUND OF THE INVENTION

1. Field of the Invention

The present invention relates to a moisture detection label, a moisture detection device, a moisture detection method, a power shutoff method, and an electronics device. In particular, the present invention relates to a moisture detection label, a moisture detection device, a moisture method, a power shutoff method, and an electronics device, each used for detecting an intrusion of a liquid into a device main body such as a portable terminal.

2. Description of the Related Art

As regards electronics devices such as cell phones, there has been proposed, for example, an electronics device having judgement label provided for detecting an intrusion of a liquid or the like into a device main body (see JP 2003-283619 A). The judgement label, as shown in FIG. 21, is made of a plastic sheet 301 on which circle patterns 307 are printed in pattern, for example, by red water-based ink. When a water droplet adheres on the circle patterns 307, the ink contained in the circle patterns 307 dissolve in the water to spread out, whereby adhesion of water can be visibly recognized.

However, according to the judgement label disclosed in JP 2003-283619 A, a user does not notice the adhesion of water unless visually identifying the label, which may lead to a case where the user keep using the cell phone. In this case, components of the cell phone are continuously supplied with power, so there is a fear that a short circuit occurs, for example.

In addition, cell phones in recent years store important data including personal information in their memories. For this reason, it is necessary to cause the cell phones to store data as soon as possible, as well as to prevent beforehand a malfunction from being caused in the cell phone due to exposure to water.

SUMMARY OF THE INVENTION

In view of the foregoing and other exemplary problems, drawbacks, and disadvantages of the conventional structures, an exemplary feature of the present invention is to provide a moisture detection label, a moisture detection device, a moisture detection method, a power shutoff method, and an electronics device.

A first object of the present invention is to provide a moisture detection label, a moisture detection device, a moisture detection method, and an electronics device, each used for reliably detecting adhesion of water eliminating a need for a visual observation of a judgment label by a user.

A second object of the present invention is to provide a power shutoff method and an electronics device, with which a malfunction due to exposure to water can be prevented beforehand.

An exemplary moisture detection label for achieving the first object of the present invention includes: a base material having an insulated front surface, at least a pair of detection terminals provided on the base material, a pattern provided on the surface of the base material and formed between the detection terminals, the pattern containing water-dispersible and conductive paint.

An exemplary moisture detection device for achieving the first object of the present invention includes: a moisture detection label that has at least a pair of detection terminals and a pattern, the detection terminals being provided on a base material with an insulated front surface, the pattern being provided on the surface of the base material and formed between the detection terminals with water-dispersible and conductive paint; and detector that detects an electrical connection state between the detection terminals of the moisture detection label.

An exemplary moisture detection method for achieving the first object of the present invention, (i) uses a moisture detection label that includes at least a pair of detection terminals and a pattern, the detection terminals being provided on a base material having an insulated front surface, the pattern containing water-dispersible and conductive paint and being formed between the detection terminals, in which (ii) the paint that swells by absorbing moisture adhered disperses toward the detection terminals, to thereby detect an electrical connection state caused between detection terminals through the paint.

An exemplary electronics device for achieving the first object of the present invention includes: a device main body having power source; a moisture detection label that is provided on the device main body, and has at least a pair of detection terminals and a pattern, the detection terminals being provided on abase material with an insulated front surface, the pattern being provided on the surface of the base material and formed between the detection terminals with a water-dispersible and conductive paint; and detector that is provided on the device main body and detects an electrical connection state between the detection terminals of the moisture detection label.

Also, an exemplary electronics device for achieving the second object of the present invention includes: a device main body having power source; a moisture detection label that is provided on the device main body and has at least a pair of detection terminals and a pattern, the detection terminals being provided on a base material with an insulated front surface, the pattern being provided on the surface of the base material and formed between the detection terminals with a water-dispersible and conductive paint; detector that is provided on the device main body and detects an electrical connection state between the detection terminals of the moisture detection label; and power shutoff means for shutting off power based on the electrical connection state detected by the detector.

An exemplary power shutoff method for achieving the second object of the present invention, (i) is used in a moisture detection label that includes at least a pair of detection terminals and a pattern, the detection terminals being provided on a base material having an insulated front surface, the pattern containing water-dispersible and conductive paint and being formed between the detection terminals, (ii) detects an electrical connection state between the detection terminals, and (iii) shuts off power in a case where it is detected that the detection terminals are electrically connected.

In the present invention, for example, when moisture adheres to the surface of the base material, conductive paint is dispersed to electrically connect between the detection terminals. Accordingly, it is possible to reliably detect adhesion of water by, for example, causing the moisture detection device to detect an electrical connection state between the detection terminals. Note that the paint is dispersed over the surface of the base material, whereby adhesion of water can be visually detected.

DETAILED DESCRIPTION OF THE EXEMPLARY EMBODIMENTS (Moisture Detection Label Construction)

Hereinafter, a moisture detection label 10 according to a first exemplary embodiment of the present invention is described based on FIGS. 1 to 6. The moisture detection label includes: a substrate 101 having a front surface 101A (including a rear surface 101B) insulated; at least a pair of detection terminals 103 and 105 provided on the substrate 101; and patterns 107 that are provided on the front surface 101A and formed between the detection terminals 103 and 105, and contain water-dispersible and conductive paint. The thin-plate-like substrate 101 is formed of an insulating resin such as polyethylene, polyethylene terephthalate, polycarbonate, or acrylonitrile-butadiene-styrene copolymer. A planar shape of the substrate 101 is square with one side length of 3 to 10 mm, for example, but may be rectangular, circular, polygonal, etc. The substrate 101 may be formed of a transparent material or a non-transparent material.

The same-shaped patterns 107 equal in shape are arranged at plural spots with their vertical lines and horizontal lines alternately shifted on the front surface 101A of the substrate 101. The patterns 107 are made of water-dispersible and conductive paint, examples of which include water-base conductive electrodeposition paint having a water dispersible property too. The electrodeposition paint is, for example, paint prepared by mixing a conductive material (ion) with ink. The patterns 107 are formed of paint with a color different from that of the substrate 101. Then, the patterns 107 are two-dimensionally dispersed and arranged.

The planar shape of the substrate 101 is circular with a diameter of 0.5 to 2 mm, for example. The patterns 107 are formed, for example, by printing the electrodeposition paint on the front surface 101A of the substrate 101 (see FIG. 3). Each of the patterns 107, namely, the paint swells to be dispersed when moisture adheres thereto.

Figure 2:
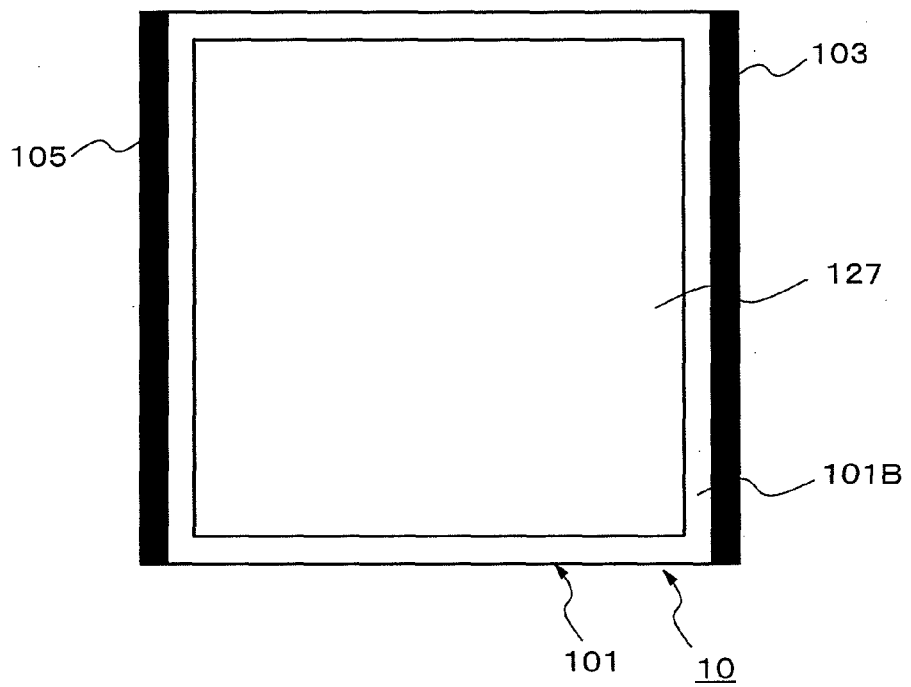
FIG. 2 shows an under surface of the moisture detection label shown in FIG. 1.

The tabular detection terminals 103 and 105 are arranged in pairs on opposing ends of the substrate 101. The detection terminals 103 and 105 are formed of a conductive material such as metal including copper, or an alloy. As shown in FIG. 2, the detection terminals 103 and 105 are structured such that detection signals are output to outside from the front surface 101A and the rear surface 101B of the substrate 101.

The detection terminals 103 and 105 each have the same length as the one side length of the substrate 101, and are attached to the substrate 101 so that all the patterns 107 are located therebetween. For example, the detection terminals 103 and 105 may be fixed to the both ends of the substrate 101 as being inserted thereto. Also, the detection terminals 103 and 105 are separated across the patterns 107.

Figure 1:
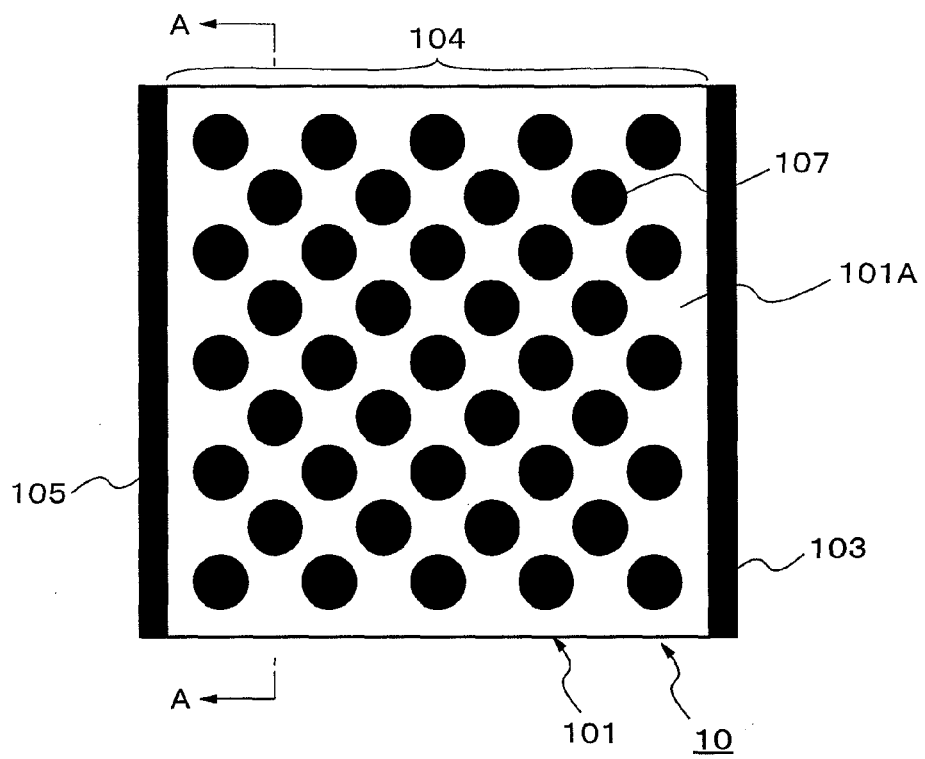
FIG. 1 is a plan view showing a first exemplary embodiment of a moisture detection label according to the present invention.
Figure 3:
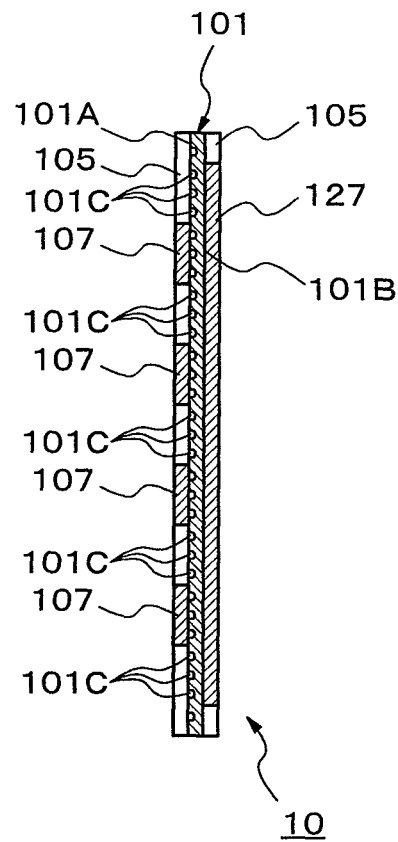
FIG. 3 is a cross-sectional view taken along the line A-A in FIG. 1.

Then, in the substrate 101, an area between the detection terminals 103 and 105 becomes a moisture detection area 104 (see FIG. 1). Also, the front surface 101A of the substrate 101 is formed such that the patterns 107 swelling by absorbing adhesion moisture disperse toward the detection terminal 103 or 105. For example, as shown in FIG. 3, the front surface 101A of the substrate 101 has plural grooves 101C at predetermined intervals across the detection terminals 103 and 105, thereby obtaining such effect that the electrodeposition paint dispersed by getting wet easily spread along the grooves 101C.

Note that a shape of the grooves 101C may be linear, curved, or polygonal. In this exemplary embodiment, the front surface 101A of the substrate 101 may be formed flat.

Even in this case, since the ink is dispersed upon getting wet, it spreads out without such grooves as described above on the front surface 101A.

Further, in this exemplary embodiment, in addition to the pair of the detection terminals 103 and 105, two detection terminals may be additionally provided. For example, the additional two detection terminals are provided on the other sides where the detection terminals 103 and 105 are not provided such that they are not connected to the detection terminals 103 and 105. If there are four detection terminals, adhesion of water is detected quickly and reliably.

As shown in FIG. 2, a sheet 127 is arranged on the rear surface 101B of the substrate 101. The sheet 127 has both surfaces coated with an adhesive etc. like a two-sided tape, with which the moisture detection label 10 is affixed to a predetermined position of an electronics device.

For example, the moisture detection label 10 is manufactured as follows. A single metal plate is bend to sandwich the front and rear surfaces of the substrate 101 on both ends, constituting the detection terminal 103. That is, the detection terminal 103 is attached along one side of the substrate 101 and the detection terminal 105 is attached along the other side thereof. Next, the electrodeposition paint is applied to predetermined spots away from the detection terminals 103 and 105 on the front surface 101A of the substrate 101, namely, the moisture detection area 104, constituting the plural patterns 107 (see FIGS. 1 and 3).

Then, the sheet 127 is affixed to the rear surface 101R of the substrate 101 (see FIGS. 2 and 3). That is, in this exemplary embodiment, the moisture detection label 10 can be easily produced. Note that the patterns 107 maybe rectangular or other shape, not necessarily being circular. The patterns are preferably circular because the wet patterns 107 easily spread (radially) in all directions.

(Moisture Detection Method)

Next, a moisture detection method using the moisture detection label 10 according to the first exemplary embodiment of the present invention is described based on FIGS. 1 and 4 to 6. In this moisture detection method, for example, the moisture detection label 10 is used which includes: at least the pair of detection terminals 103 and 105 provided on the substrate 101 having the insulated front surface 101A; and the patterns 107 that are provided on the front surface 101A of the substrate 101 and formed between the detection terminals 103 and 105, and contain water-dispersible and conductive paint. The paint that swells by absorbing adhesion moisture disperses toward the detection terminals 103 and 105. Then, electrical connection caused between the detection terminals 103 and 105 through the paint is detected.

Figure 4:
FIG. 4 is an equivalent circuit diagram schematically showing the moisture detection label shown in FIG. 1 as an electronic circuit.

When moisture does not adhere to the patterns 107 of the moisture detection label 10, as shown in FIGS. 1 and 4, there is no electrical connection between the detection terminals 103 and 105, with no current flowing therebetween.

Figure 5:
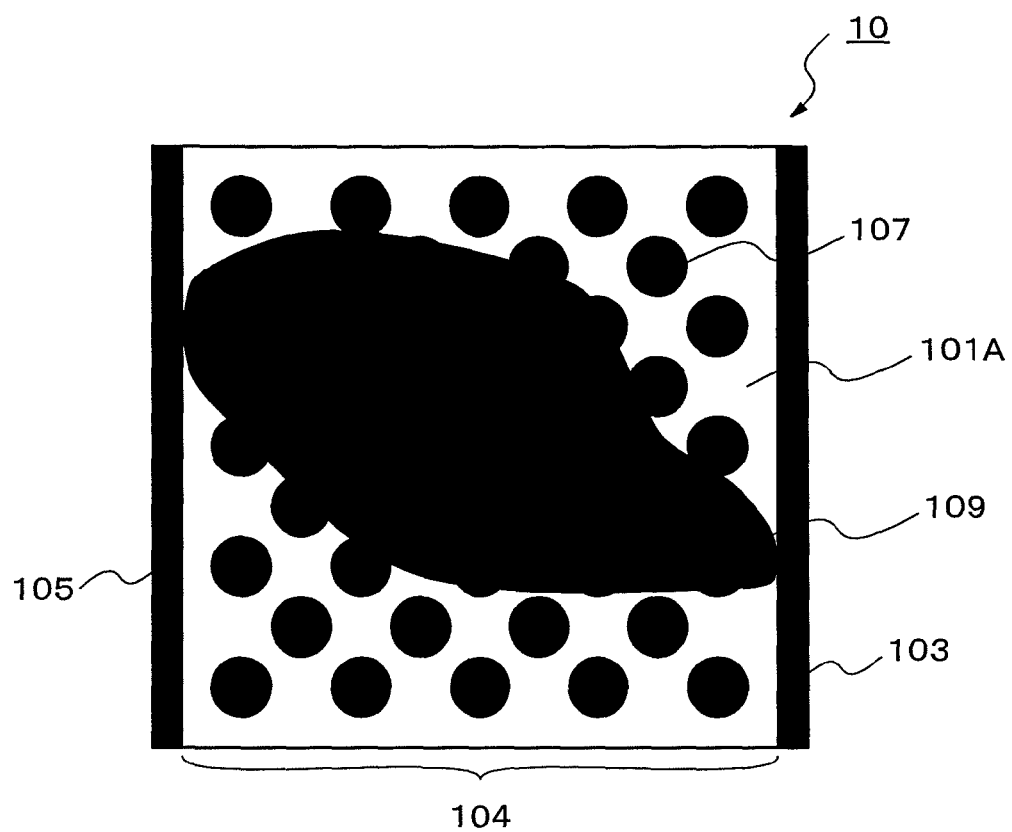
FIG. 5 is a plan view showing a state in which paint contained in patterns is dispersed in the moisture detection label in FIG. 1.

On the other hand, when moisture adheres to the patterns 107 of the moisture detection label 10, as shown in FIG. 5, the patterns (paint) 107 swell and disperse, thereby spreading (seeping) out to the moisture detection area 104. The substrate 101 has the plural grooves 101C between the detection terminals 103 and 105, whereby the patterns (paint) 107 quickly and reliably disperse to the detection terminal 103 or 105.

Figure 6:
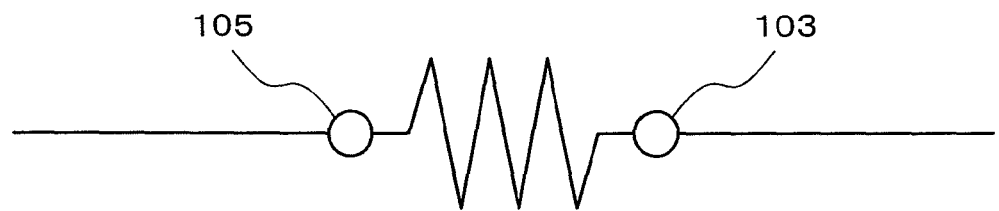
FIG. 6 is an equivalent circuit schematically showing the moisture detection label shown in FIG. 5 as an electronic circuit.

A moisture-adhered area 109 expands by the seeping patterns (paint) 107 and the conductive paint connects the detection terminals 103 and 105. That is, as shown in FIG. 6, the detection terminals 103 and 105 are electrical connected with a resistance value of the ink. In this exemplary embodiment, the existence of adhesion of moisture is judged by detecting the electrical connection state between the detection terminals 103 and 105.

Even when moisture adheres to the patterns (paint) 107, such a case may happen that the paint do not spread across the detection terminals 103 and 105. In this exemplary embodiment, moisture deposition at such a level that the paint does not connect the detection terminals 103 and 105 is not regarded as a water adhesion state.

In the moisture detection label 10, when the front surface 101A of the substrate 101 gets wet in water, the paint in the patterns seeps out from the patterns and the planer shape of the patterns 107 changes. Accordingly, as shown in FIG. 5, the planer shape of the patterns 107 changes upon moisture deposition thereon. Therefore, adhesion of water can be visually detected with ease. Also, in the moisture detection label 10, the moisture-adhered area 109 expands when moisture adheres to the patterns 107, to thereby electrically connect the detection terminals 103 and 105 (see FIG. 6), leading to a change in the resistance value.

Thus, water leak is electrically detected using the moisture detection label 10 in this exemplary embodiment.

Therefore, and if the moisture detection label 10 is arranged in the electronics device, adhesion of water to the electronics device can be reliably detected.

Note that in this exemplary embodiment, since the patterns 107 are arranged with their vertical lines and horizontal lines alternately shifted, when moisture adheres to the patterns (paint) 107, paint is reliably dispersed and the moisture-adhered area 109 expands. Also, in this exemplary embodiment, the detection terminals 103 and 105 are arranged along the entire sides of the substrate 101 on the both ends. Even when moisture adheres to the patterns (paint) 107, adhesion of water can be reliably detected.

In this exemplary embodiment, the shape of the substrate 101, the shape or arrangement of the patterns 107 or the detection terminal 103 (105), or the like can be changed as appropriate.

FIGS. 7 to 11 are plan views of a moisture detection label according to second to sixth exemplary embodiments of the present invention. Note that in the second to fourth exemplary embodiments shown in FIGS. 7 to 9, parts corresponding to those of FIG. 1 are denoted by the same reference numerals and a detailed description thereof is omitted.

Figure 7:
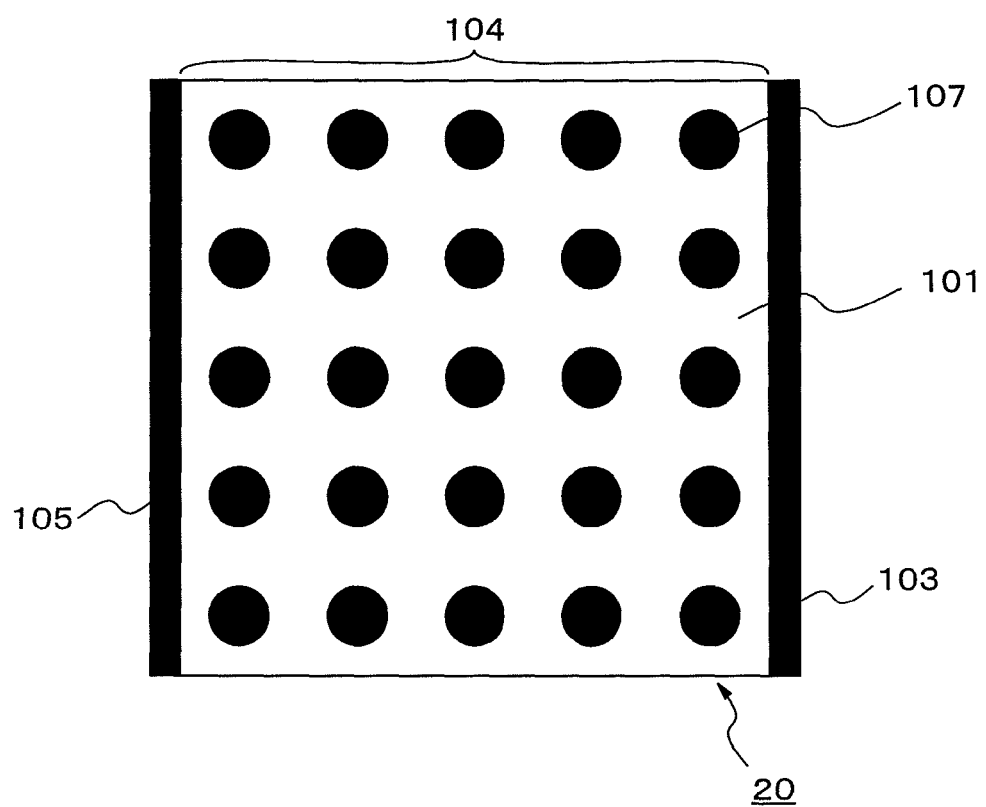
FIG. 7 is a plan view showing a second exemplary embodiment of the moisture detection label according to the present invention.

For example, as shown in FIG. 7, the patterns 107 of a moisture detection label 20 are arranged with their vertical lines and horizontal lines aligned. Other constructions (for example, the grooves are formed across the detection terminals), actions, and effects are the same as those of the exemplary embodiment of FIG. 1.

Figure 8:
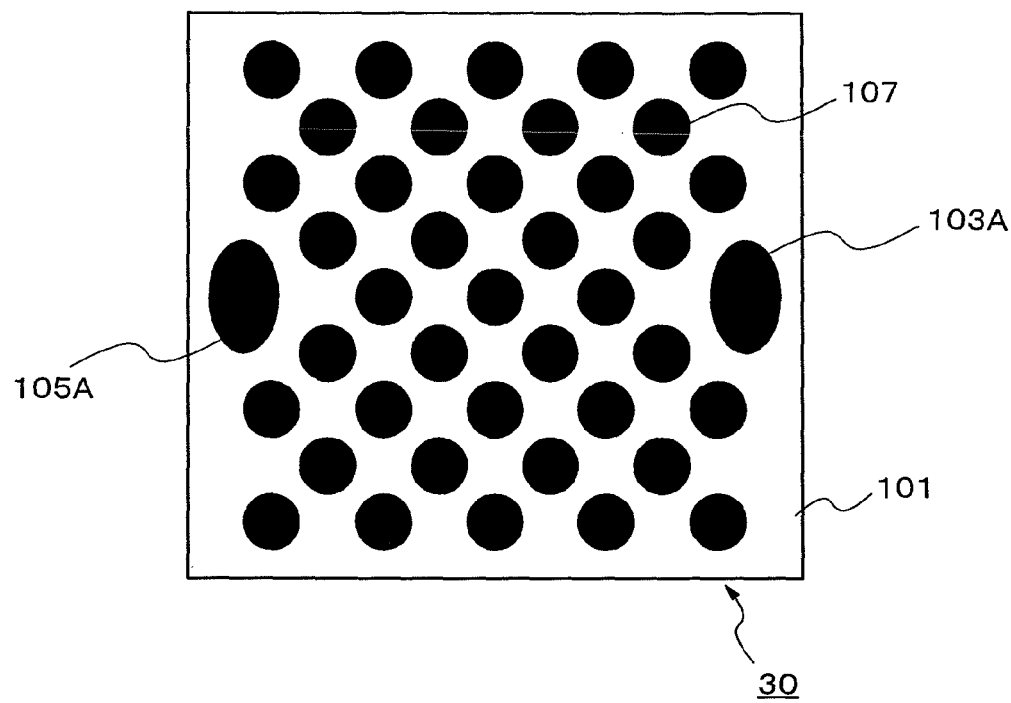
FIG. 8 is a plan view showing a third exemplary embodiment of the moisture detection label according to the present invention.

As shown in FIG. 8, a planer shape of detection terminals 105A and 103A in a moisture detection label 30 may have an elliptic shape vertically elongated. In this case, the detection terminals 105A and 103A are embedded in the substrate 101 while the front and rear surfaces thereof are exposed from the front and rear surfaces of the substrate 101. Accordingly, also in the exemplary embodiment of FIG. 8, an electrical connection state between the detection terminals 105A and 103A can be detected from the rear surface of the substrate 101.

Note that in the third exemplary embodiment shown in FIG. 8, the detection terminals 105A and 103A each arranged substantially at each of the centers of both ends of the moisture detection label 30. Other constructions and action effects are the same as those of the exemplary embodiment of FIG. 1.

Figure 9:
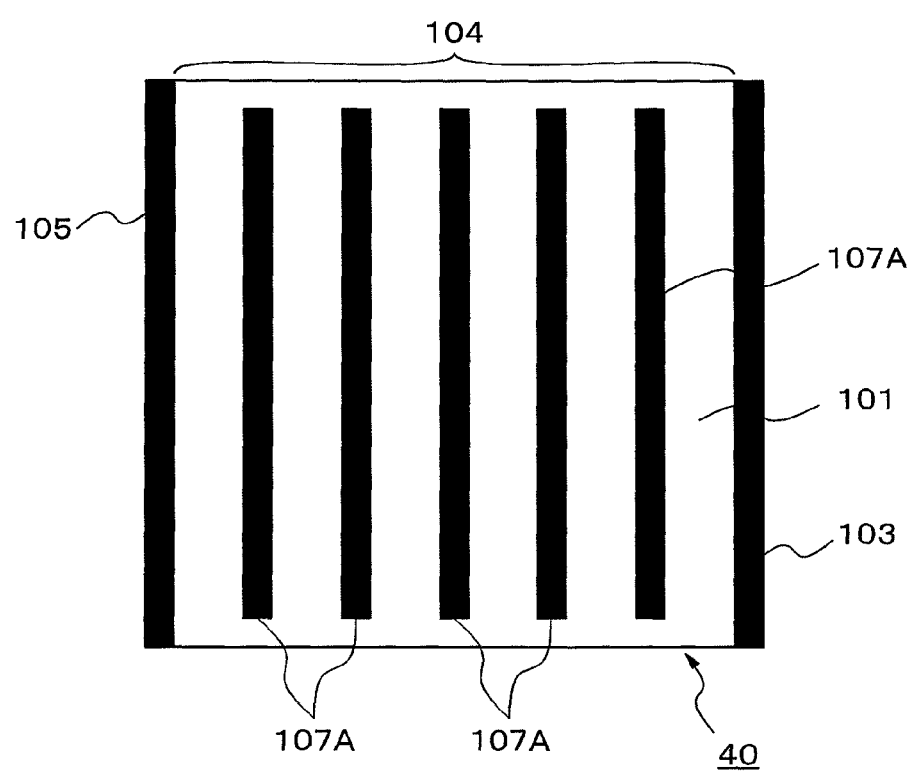
FIG. 9 is a plan view showing a fourth exemplary embodiment of the moisture detection label according to the present invention.

As shown in FIG. 9, a planer shape of patterns 107A in a moisture detection label 40 may be stripes, for example. In this case, the plural patterns 107A are arranged in parallel to the detection terminals 103 and 105 at equal intervals. Other constructions and action effects are the same as those of the exemplary embodiment of FIG. 1.

Figure 10:
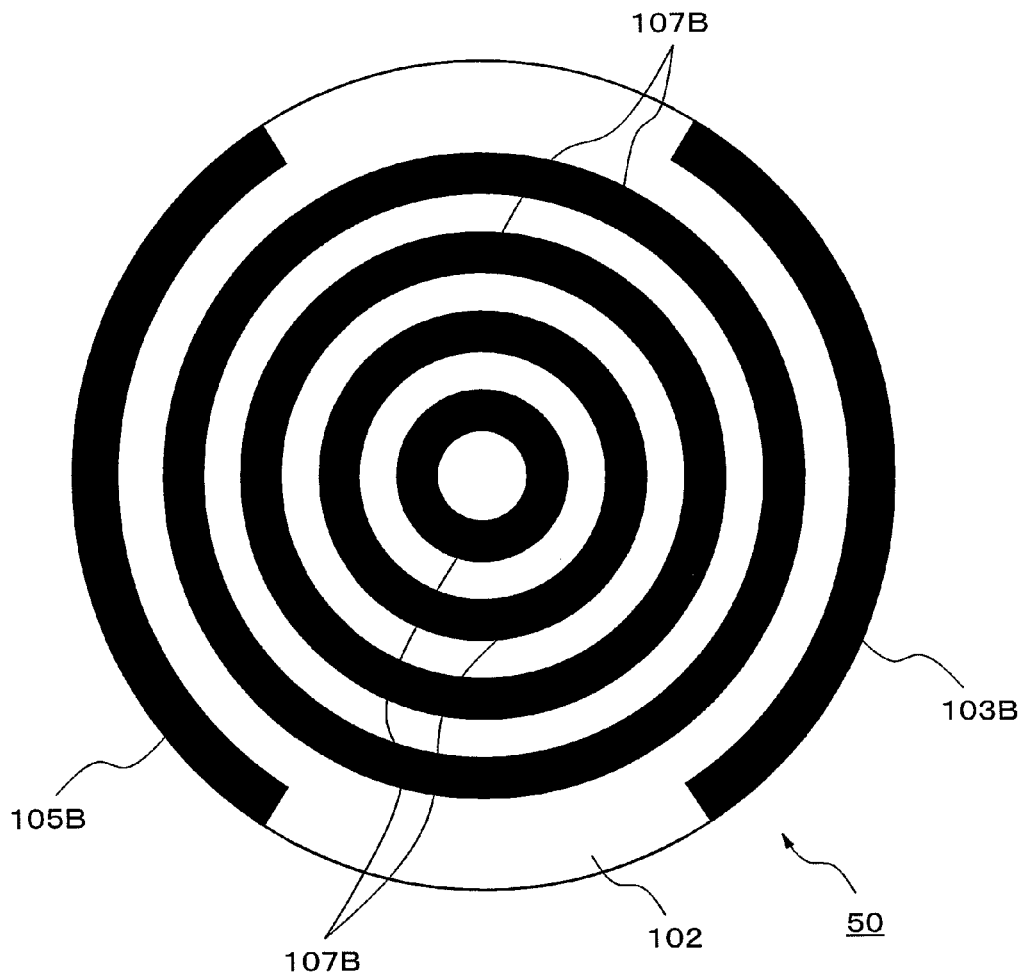
FIG. 10 is a plan view showing a fifth exemplary embodiment of the moisture detection label according to the present invention.

As shown in FIG. 10, a planer shape of a substrate 102 in a moisture detection label 50 may be circular and a planer shape of patterns 107B may be rings. In this case, the plural rings 107B are arranged at equal intervals to be concentric to the center of the moisture detection label 50.

Also, in the moisture detection label 50 of FIG. 10, a pair of detection terminals 103B and 105B are made arcs along an outer periphery of the substrate 102. According to the fifth exemplary embodiment shown in FIG. 10, the substrate 102 has a disc shape, and therefore the moisture detection label 50 can be made smaller than the angular moisture detection labels 10, 20, 30, and 40 (see FIGS. 1 and 7 to 9). Other constructions and action effects are the same as those of the exemplary embodiment of FIG. 1.

Figure 11:
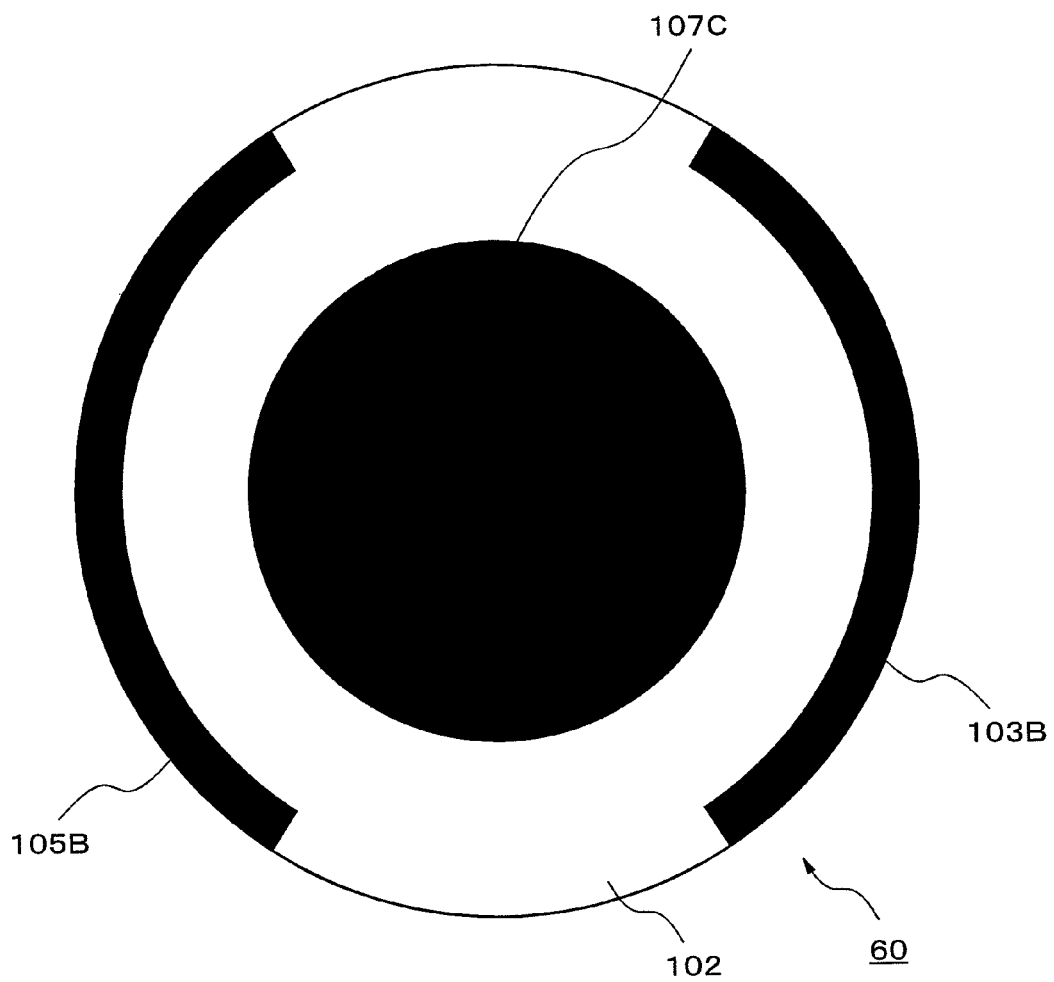
FIG. 11 is a plan view showing a sixth exemplary embodiment of the moisture detection label according to the present invention.

As shown in FIG. 11, a planer shape of a pattern 107C in a moisture detection label 60 may be circular, for example. Note that for the construction of the sixth exemplary embodiment shown in FIG. 11, parts corresponding to those of FIG. 10 are denoted by the same reference numerals and a detailed description thereof is omitted in FIG. 11.

In this exemplary embodiment, the number of the pattern 107C can be set to one. Other constructions and action effects are the same as those of moisture detection label 50 of FIG. 10.

(Moisture Detection Device Construction)

A moisture detection device according to a first exemplary embodiment of the present invention (see FIG. 12) has one of the moisture detection labels 10, 20, 30, 40, 50, and 60 shown in FIGS. 1 and 7 to 9 mounted thereto. The moisture detection labels shown in FIG. 12 are denoted by reference numeral 100 (100a, 100b, 100c, and 100d) to be described.

A moisture detection device 110 of this exemplary embodiment includes: at least a pair of detection terminals provided on a substrate having an insulated front surface; four moisture detection labels 100 that are provided on the front surface of the substrate and formed between the detection terminals, and contain water-dispersible and conductive paint; and a current detector 116 (detection means) for detecting an electrical connection state between the detection terminals of the moisture detection labels 100.

Figure 12:
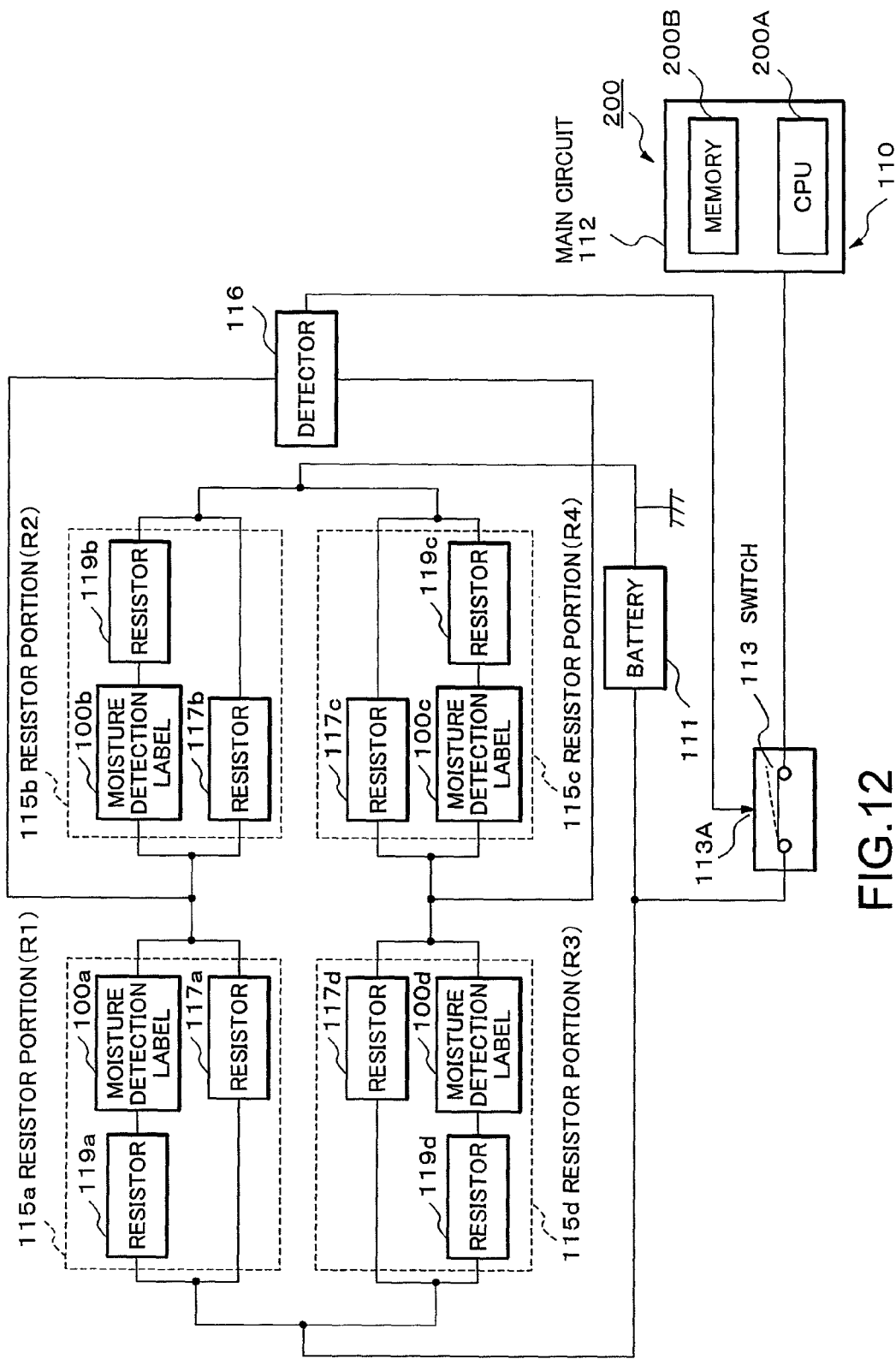
FIG. 12 is a block diagram showing a first exemplary embodiment of a moisture detection device according to the present invention.

As shown in FIG. 12, the moisture detection device 110 of this exemplary embodiment further includes four resistor portions 115a, 115b, 115c, and 115d, which are connected circularly. That is, the moisture detection device 110 is an example using a Wheatstone bridge.

The resistor portions 115a, 115b, 115c, and 115d have first resistors 117a, 117b, 117c, and 117d, respectively. The first resistors 117a to 117d have the same resistance values.

Thus, when the moisture detection labels 100 are not wet in water (specifically, a non-electrically-connected state shown in FIGS. 1 and 4), the resistor portions 115a to 115d are in a balanced state due to setting (the same resistance values) of the first resistors 117a to 117d. Here, the balanced state of the Wheatstone bridge means a state where no current flows into the current detector 116 while the resistor portions 115a (R1), 115b (R2), 115c (R3), and 115d (R4) shown in FIG. 12 have a relation of R1/R2=R3/R4.

In the resistor portion 115a, a second resistor 119a and the moisture detection label 100a, which are connected in series, are connected to the first resistor 117a in parallel. In the resistor portion 115b, a second resistor 119b and the moisture detection label 100b, which are connected in series, are connected to the first resistor 117b in parallel. In the resistor portion 115c, a second resistor 119c and the moisture detection label 100c, which are connected in series, are connected to the first resistor 117c in parallel. In the resistor portion 115d, a second resistor 119d and the moisture detection label 100d, which are connected in series, are connected to the first resistor 117d in parallel.

The second resistors 119a, 119b, 119c, and 119d are set to have different values. When the moisture detection labels 100a to 100d get wet nearly simultaneously (for example, when the moisture detection device 110 is dropped in a puddle), the resistor portions 115a to 115d have different resistance values, whereby the Wheatstone bridge is non-equilibrium.

In the resistor portions 115a to 115d, the resistance values change according to the non-electrically-connected state (see FIGS. 1 and 4) or the electrically-connected state (see FIGS. 5 and 6) of the moisture detection labels 100a to 100d. When the moisture detection labels 100a to 100d are in the electrically-connected state (see FIGS. 5 and 6), the resistance values of resistor portions 115a to 115d change, whereby the Wheatstone bridge is non-equilibrium.

Here, the non-balanced state of the Wheatstone bridge means a state where a current flows into the current detector 116 while the four resistor portions R1 to R4 constituting the Wheatstone bridge do not have the relation of R1/R2=R3/R4.

The moisture detection device 110 includes the current detector 116 as the detection means. The current detector 116 connects a connection line between the resistor portions 115a and 115b to a connection line between the resistor portions 115c and 115d. The current detector 116 is connected to a switch 113 as power shutoff means. The switch 113 is connected to a main circuit 112 of an electronics device 200 to which the moisture detection device 110 is mounted (see FIG. 18). The main circuit 112 includes a CPU (control means) 200A, a memory (storage means) 200B, a communication circuit (not shown) such as a speaker.

The moisture detection device 110 further includes a battery 111 for power supply. The battery 111 connects the connection line between the resistor portions 115a and 115d to the connection line between the resistor portions 115b and 115c.

The battery 111 may be used as a battery for the electronics device 200.

The switch 113 is connected between the battery 111 and the main circuit 112. Accordingly, when the switch 113 is open, power of the battery 111 is not supplied to the main circuit 112.

(Moisture Detection Device Action)

Figures 13, 14:
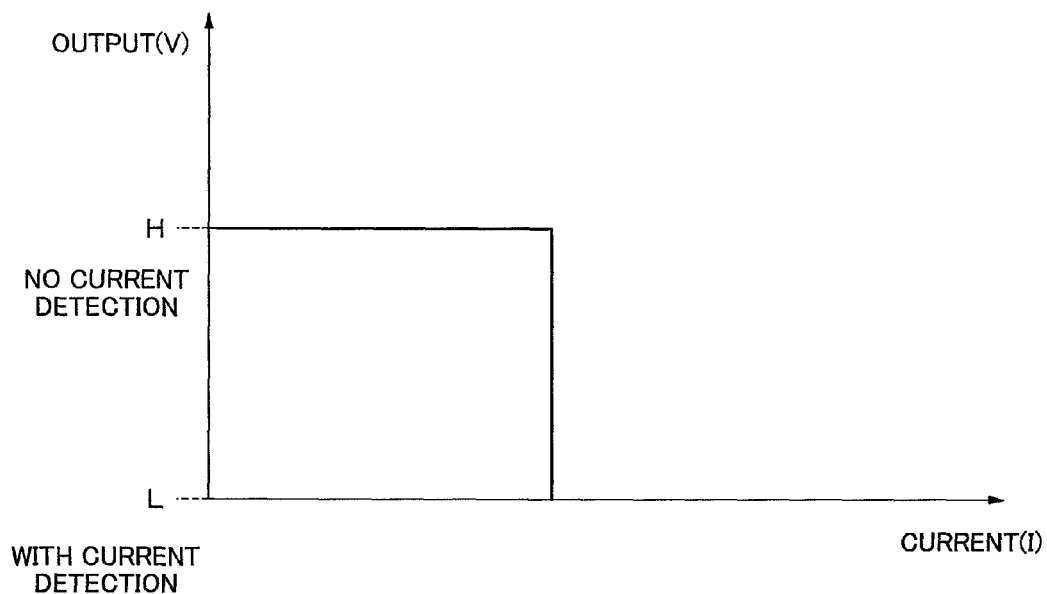
FIG. 13 is a graph showing a relationship between an output voltage and an amount of output power at a current detector in the moisture detection device shown in FIG. 12.
FIG. 14 is a table showing a relationship between an input voltage and a switching operation at a switch in the moisture detection device shown in FIG. 12.

An action of the moisture detection device 110 shown in FIG. 12 is described based on FIGS. 13 and 14. The moisture detection device 110 using the Wheatstone bridge that causes a current to flow when a resistant balance is lost, in which the current detector 116 detects changes in resistant values of the resistor portions 115a and 115b.

FIG. 13 is a drawing explaining an operation of the current detector 116. The current detector 116 detects a current (I) from the Wheatstone bridge and then sets a switch control output voltage value to be output to the switch 113 to 0 V ("L" signal) (see FIG. 13). Whereas when the current detector 116 does not detects the current (I) from the Wheatstone bridge, the switch control output voltage value to be output to the switch 113 is set to 1 V ("H" signal) (see FIG. 13).

FIG. 14 is a drawing explaining an operation of the switch 113. The switch 113 shown in FIG. 12 includes a control terminal 113A to which the current detector 116 is connected. When the "H" signal is input to the control terminal 113A from the current detector 116, the switch 113 is turned on (a state indicated by the real line of FIG. 12) and power of the battery 111 is supplied to the main circuit 200.

On the other hand, when the "L" signal is input to the control terminal 113A from the current detector 116, the switch 113 is turned off (a state indicated by the imaginary line of FIG. 12) to interrupt the voltage circuit of the battery 111. As a result, power is not supplied to the main circuit 200.

Since the moisture detection device 110 uses the Wheatstone bridge, when no moisture adheres to the moisture detection labels 100a to 100d (the non-electrically-connected state shown in FIGS. 1 and 4), the resistor portions 115a to 115d are in the balanced state. Therefore, the current detector 116 detects no current, and the switch is ON. Note that the moisture detection method using the moisture detection label 10 described based on FIGS. 1 and 4 to 6 is applied to the moisture detection device 110.

On the other hand, when moisture adheres to any of the moisture detection labels 100a to 100d (the electrically-connected state shown in FIGS. 5 and 6), a current flows between the seals 100 in the electrical connection state and the resistant portions 119 (any of the resistors 119a to 119d), whereby any of the resistance values of the resistor portions 115a to 115d) changes.

Accordingly, the Wheatstone bridge is non-equilibrium, and a current flows into the current detector 116. At this time, the current detector 116 outputs the "L" signal to the control terminal 113A of the switch 113 to turn the switch 113 OFF from ON. When the switch 113 is turned off, the power supply to the main circuit 112 from the battery 111 is shut off.

Note that in the moisture detection device 110, by visually identifying the moisture detection labels 100, it is possible to specify which detection seal gets wet in water.

According to the construction of this exemplary embodiment, power supply to the main circuit 112 is immediately shut off in conjunction with the moisture-adhesion states of the moisture detection labels 100a to 100d (the electrically-connected state shown in FIGS. 5 and 6), thereby making it possible to prevent a short circuit or the like from being caused by moisture adhesion to the main circuit 112. Therefore, according to this exemplary embodiment, generation of failure due to exposure to water or the like can be prevented.

Also, the moisture detection device 110 has the construction using the four moisture detection labels 100, thereby providing the moisture detection labels 100 at plural locations of the electronics device. Accordingly, adhesion of water to the electronics device can be detected reliably, and the location of the adhesion of water can be specified. Further, according to this exemplary embodiment, even when the four moisture detection labels 100 are arranged, only one detection circuit (the current detector 116) is provided, so the construction can be preferably simplified and the mounting area may be preferably set small.

Figure 15:
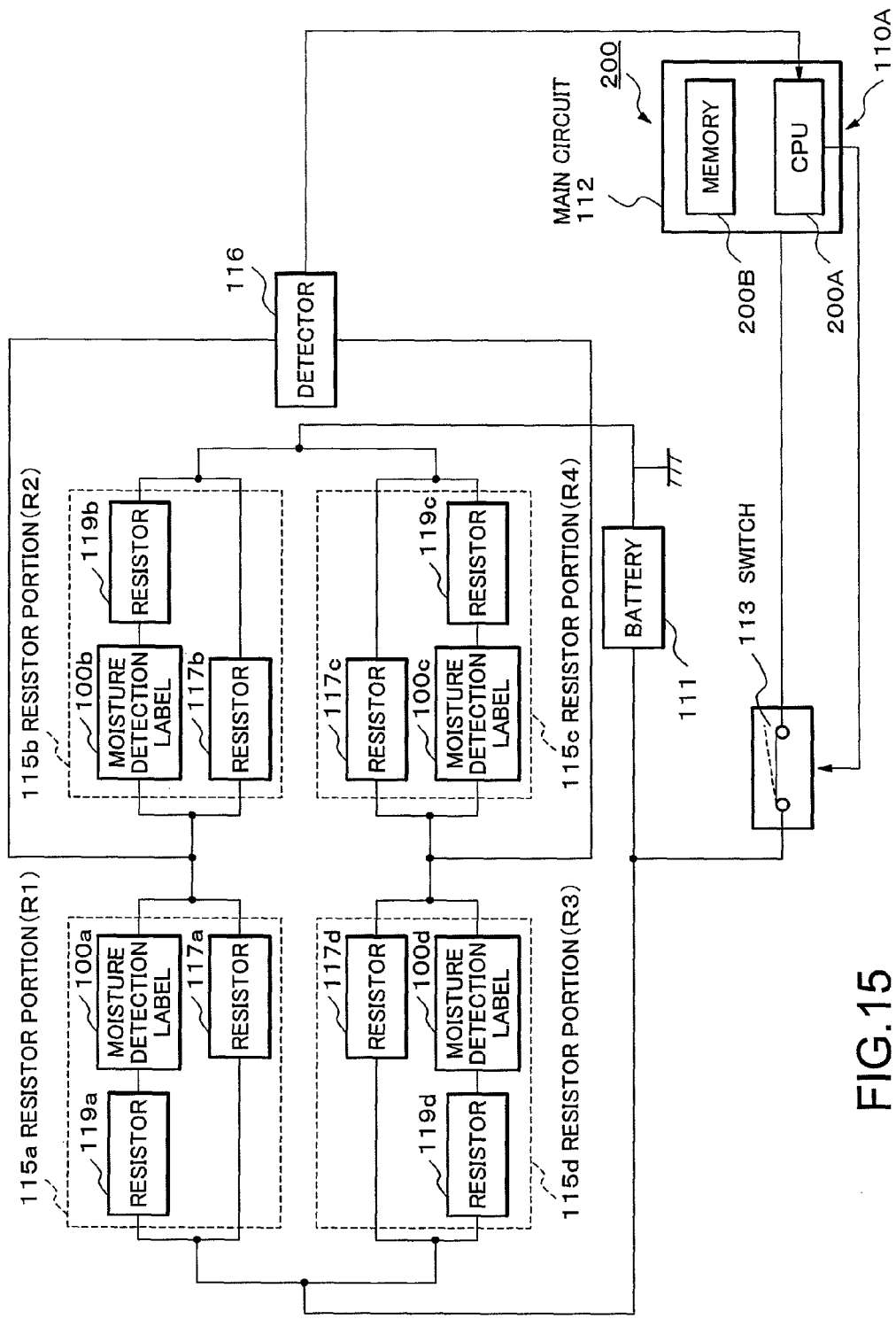
FIG. 15 is a block diagram showing a second exemplary embodiment of the moisture detection device according to the present invention.

FIG. 15 shows a moisture detection device according to a second exemplary embodiment of the present invention. Note that in the construction of the second exemplary embodiment, parts corresponding to those of FIG. 12 are denoted by the same reference numerals in FIG. 15, and a detailed description thereof is omitted. In the moisture detection device 110 of this exemplary embodiment, an output terminal of the current detector 116 is connected to the CPU 200A of the electronics device 200, and the CPU 200A is connected to the switch 113. Other constructions are the same as those of the exemplary embodiment shown in FIG. 12.

Figure 16:
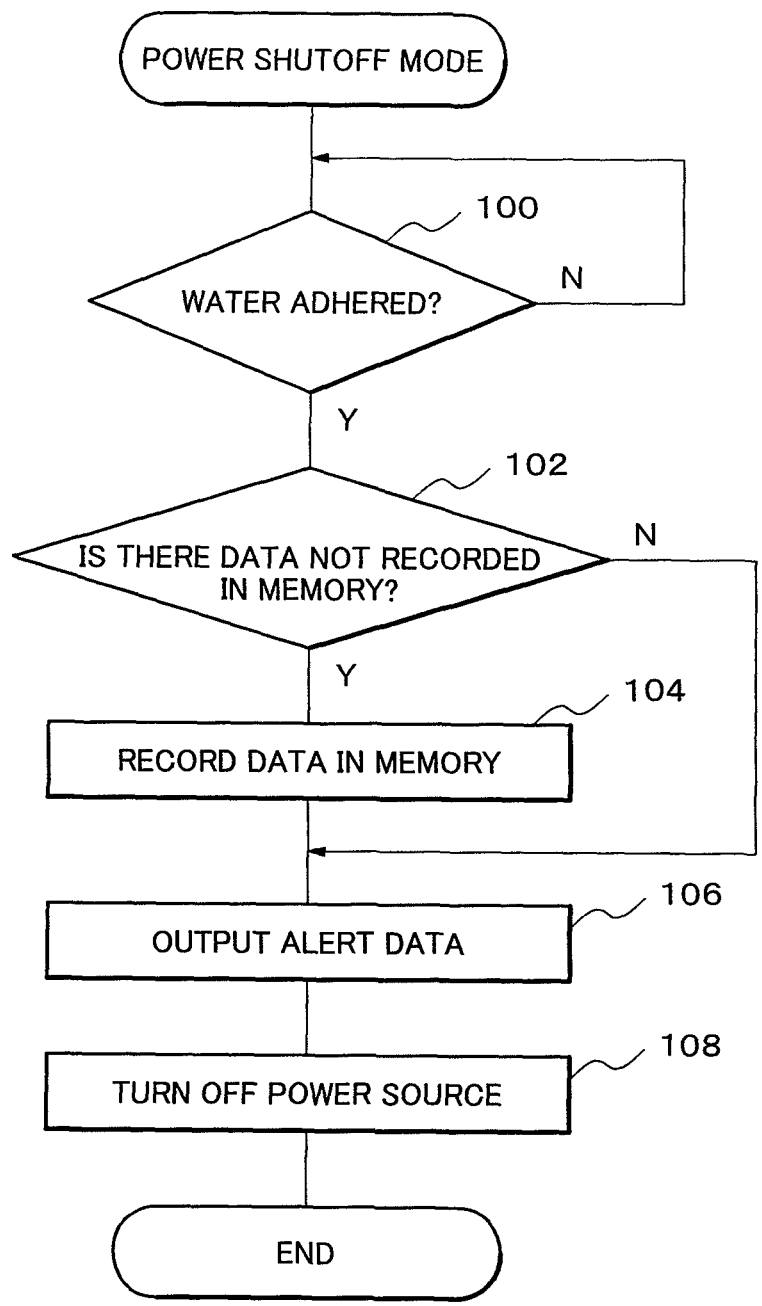
FIG. 16 is a flowchart showing a process flow of controlling power in the moisture detection device shown in FIG. 15.

Next, a power shutoff method of this exemplary embodiment is described based on FIG. 16. This power shutoff method is used for the moisture detection labels 100 that include the patterns having at least a pair of detection terminals provided on the substrate having the front surface insulated and formed between the detection terminals, and contain the water-dispersible and conductive paint, in which an electrical connection state between the detection terminals is detected, and when the electrical connection therebetween is detected, power to the main circuit 112 is shutoff.

Referring to FIG. 16, a processing relating to a power shutoff mode in the electronics device 200 is described. Here, the processing (power shutoff mode) in the electronics device 200 is represented by a flow chart of FIG. 16 executed in the CPU 200A of the electronics device 200 shown in FIG. 15. Programs thereof are previously stored in a program area of the memory 200B (see FIG. 15).

As shown in FIG. 16, in a step 100, the CPU 200A judges whether or not the moisture detection labels 100 indicate a water-adhesion state (the electrically-connected state shown in FIGS. 5 and 6), based on the "L" signal from the current detector 116. When YES in a step 100, that is, it is judged that the moisture detection labels 100 are in the electrical connected state, the CPU 200A judges in a step 102 whether there is data that has not been recorded in the memory 200B yet.

When YES in the step 102, that is, it is judged that there is data that has not been recorded therein yet, the CPU 200A records in a step 104 the data in the memory 200B. After the processing in the step 104, the CPU 200A causes a speaker (alert means) (not shown) in a step 106 to output alert data such as an alert sound or message for a predetermined time. Note that in this case, a display 202 of the electronics device 200 (see FIG. 18) may be caused to display an alert message, etc.

After the processing in the step 106, the CPU 200A turns the switch 113 OFF from ON to thereby turn off the power in a step 108. On the other hand, when NO in a step 102, that is, it is judged that all data is recorded in the memory 200B, the processing advances to the step 106 where the CPU 200A causes the speaker to output the alert data and to turn off the power in the step 108. Other action effects are the same as those of the exemplary embodiment of FIG. 12. Note that in this exemplary embodiment, the power may be turned off without recording data in the memory 200B or causing the speaker or the like to output alert data.

Figure 17:
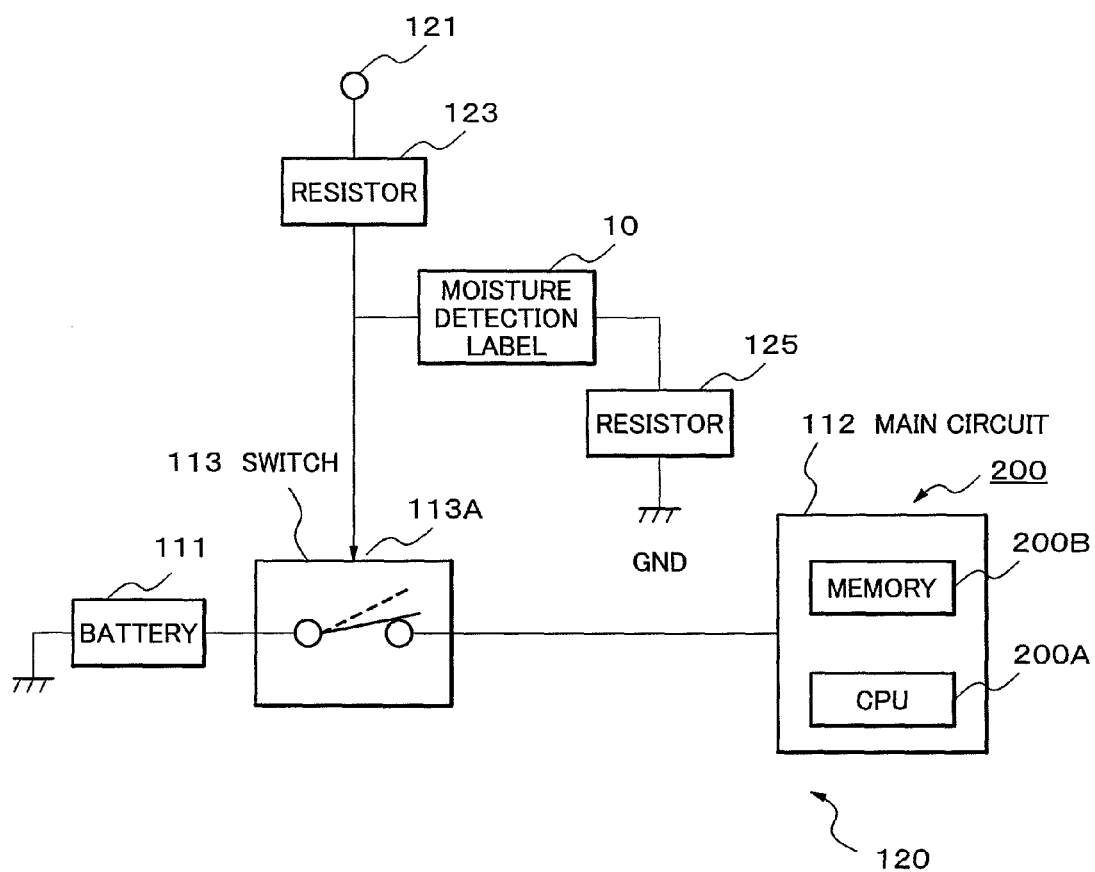
FIG. 17 is a block diagram showing a third exemplary embodiment of the moisture detection device according to the present invention.

FIG. 17 shows a moisture detection device according to a third exemplary embodiment of the present invention. Note that in the construction of the third exemplary embodiment, parts in FIG. 17 corresponding to those of FIG. 12 are denoted by the same reference numerals and a detailed description thereof is omitted.

A moisture detection device 120 shown in FIG. 17 includes the battery 111, the main circuit 112, the switch 113, the moisture detection label 10, an output terminal 121 of a regulator, and resistors 123 and 125. In the moisture detection device 120, the switch 113 is connected in series between the battery 111 and the main circuit 112. Here, the moisture detection label mounted to the moisture detection device 120 is, for example, the moisture detection label 10 shown in FIG. 1.

Then, the resistor 123 is connected in series between the output terminal 121 of the regulator and the switch 113. Further, the moisture detection label 10 and the resistor 125 are connected between the resistor 123 and the switch 113.

In the moisture detection device 120, when no moisture adheres to the moisture detection label 10 (the non-electrically-connected state shown in FIGS. 1 and 4), the control terminal 113A of the switch 113 is pulled up by the output terminal 121 of the regulator (power source). Accordingly, the switch 113 is ON, whereby power is supplied from the battery 111 to the main circuit 112.

On the other hand, when moisture adheres to the moisture detection label 10 (the electrically-connected state shown in FIGS. 5 and 6), a current is pulled down to GND (ground) through the resistor 125. Thus, a voltage is not applied to the control terminal 113A of the switch 113, and the switch 113 is turned OFF from ON, whereby power supply from the battery 111 to the main circuit 112 is shutoff.

Also, in the moisture detection device 120 shown in FIG. 17 too, similar to the case of the moisture detection device 110 shown in FIG. 12, the electrical connection state of the moisture detection label 10 can be detected based on a resistor value change. Then, based on the detection result, power supply to the main circuit 112 can be shutoff.

Also, the moisture detection device 120 can detect adhesion of water with a still simpler construction than the moisture detection device 110 shown in FIG. 12.

The above detection devices are preferably used for electronics devices having a data storage function, such as a cell phone (mobile terminal), a portable personal computer, PDA (Personal Digital Assistant), and various cameras.

(Electronics Device Construction)

Electronics devices according to this exemplary embodiment (see FIGS. 18 and 19) have one of the moisture detection devices 110, 110A, and 120 shown in FIGS. 12, 15, and 17. Note that the electronics device in this exemplary embodiment is a cell phone for description. Also, the electronics device in this exemplary embodiment is described as an example having the moisture detection device 110 shown in FIG. 12 mounted thereto.

The electronics device includes: a device main body having a power source; the moisture detection label that includes the patterns having at least a pair of detection terminals arranged on the device main body, provided on the substrate having the insulated front surface, and formed between the detection terminals, and contain the water-dispersible and conductive paint; and detector arranged on the device main body, for detecting an electrical connection state between the detection terminals of the moisture detection label.

Figure 18:
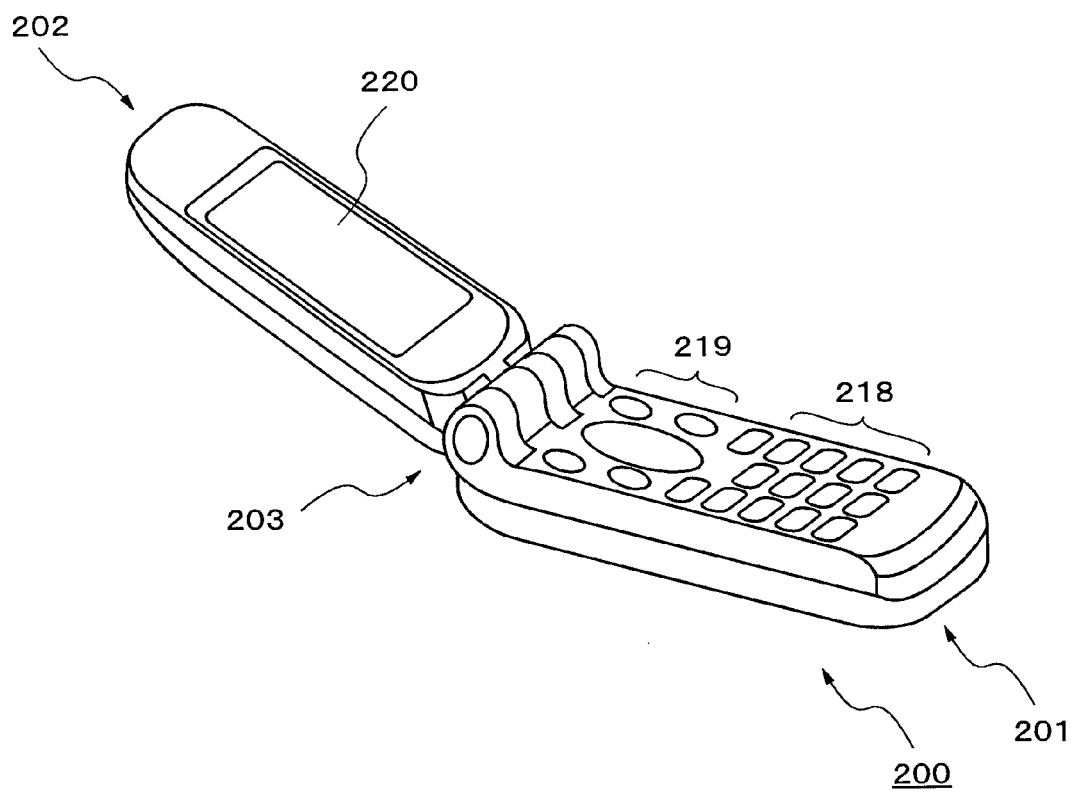
FIG. 18 is a perspective view of a first exemplary embodiment of a cell phone according to the present invention.
Figure 19:
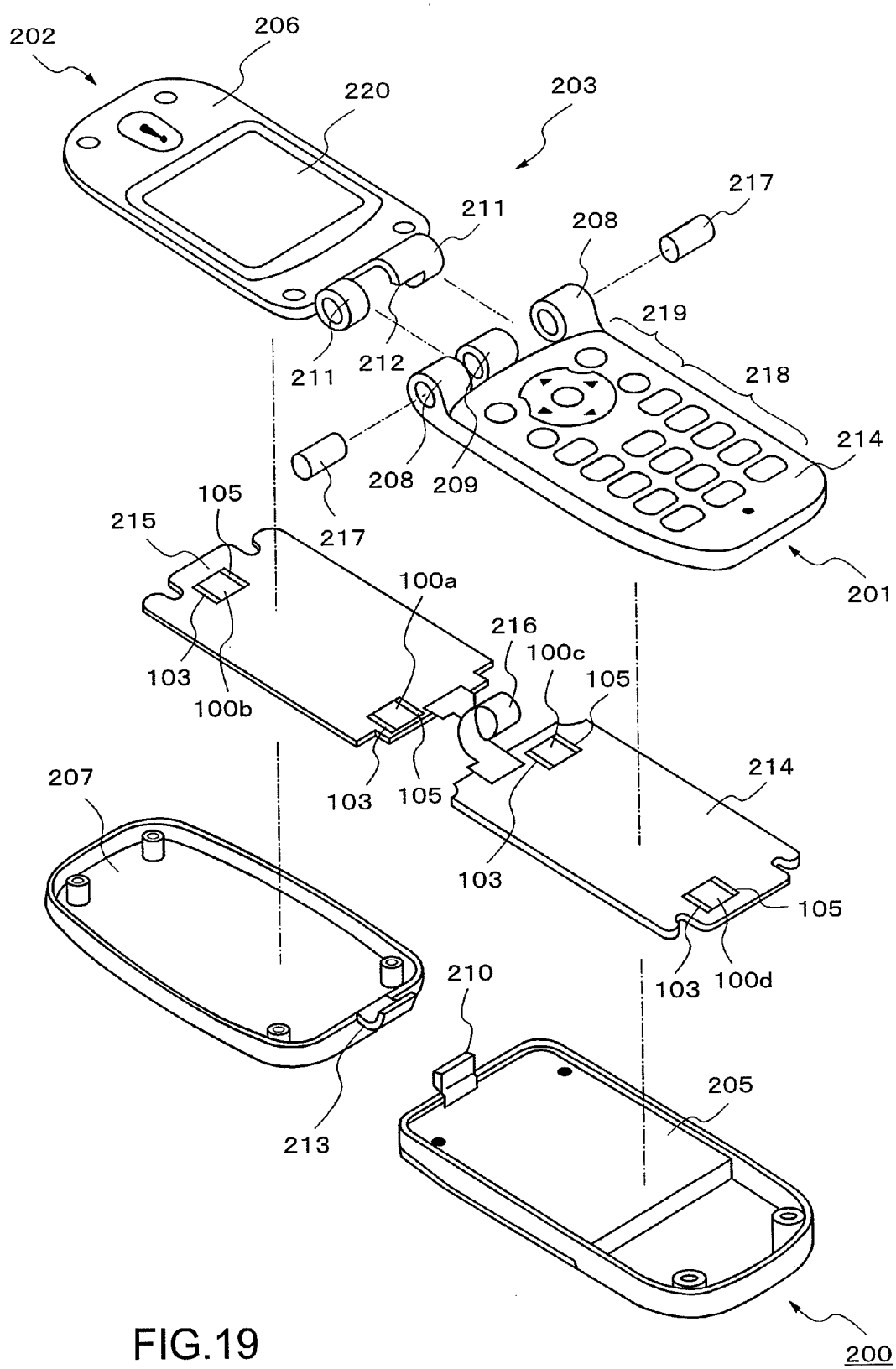
FIG. 19 is an exploded perspective view showing the cell phone shown in FIG. 18.

FIG. 18 is a perspective view when a foldable cell phone 200 is opened. FIG. 19 is an exploded perspective view of the foldable cell phone 200 shown in FIG. 18.

As shown in FIG. 18, the display portion (device main body) 202 of the mobile phone 200 and an operation portion (device main body) 201 are openable and closable via a hinge portion. As shown in FIG. 19, the operation portion (device main body) 201 includes an upper case 204 and a lower case 205, which are formed like a shallow box. The operation portion 201 accommodates a print wiring board 214. The upper case 204 includes a predetermined number of function buttons 219 and push-button dial 218.

The display portion 202 includes an upper case 206 and a lower case 207 similarly to the operation portion 201. The display portion 202 accommodates a print wiring board 215. The upper case 206 includes a display 220 as alert means.

The print wiring board 214 and the print wiring board 215 are connected through a flexible board 216. The hinge portion 203 is composed of hinge barrels 208 and 211, half hinge barrels 209, 210, 212, and 213, and a hinge unit 217.

In this exemplary embodiment, the moisture detection labels 100a to 100d are arranged at four locations of the print wiring board 214. For example, the moisture detection labels 100a to 100d are respectively arranged near the hinge portion 203 and its opposite side through which a liquid such as water easily enters.

In this exemplary embodiment, the plural moisture detection labels 100, for example, four seals, are arranged. Thus, it is possible to specify which location of the cell phone 200 got wet in water by visually identifying the moisture detection labels 100. Note that other actions and effects are the same as those of the moisture detection device shown in FIG. 12, so the detailed description thereof is omitted.

Figure 20:
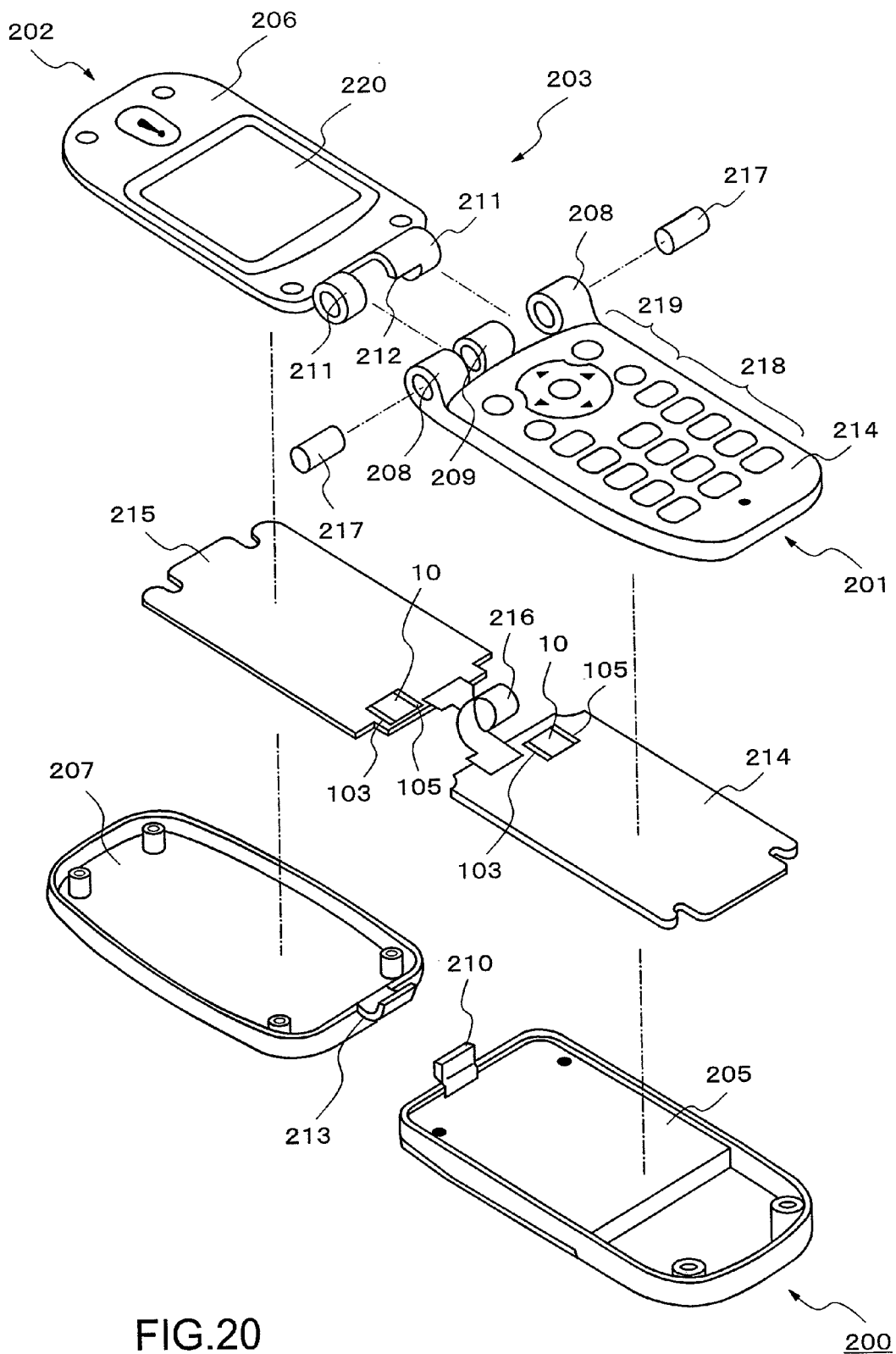
FIG. 20 is an exploded perspective view of a second exemplary embodiment of the cell phone according to the present invention.
Figure 21:
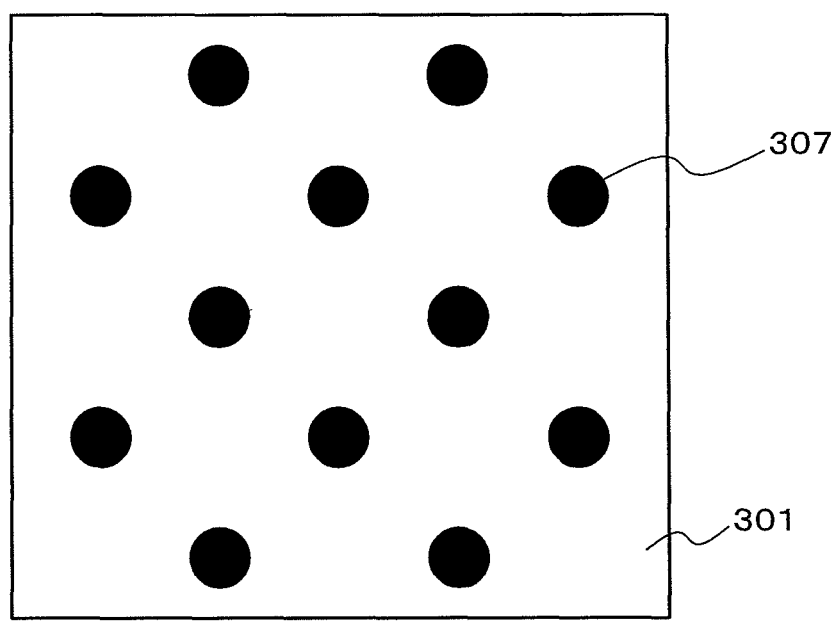
FIG. 21 is a plan view of a conventional judgment label.

Note that in this exemplary embodiment, the arrangement locations and number of the moisture detection labels 100 can be changed appropriately. For example, the seal may be arranged on a front surface of the lower case 205. Also, as shown in FIG. 20, in the mobile phone 200, the moisture detection labels 100 may be arranged at only two locations near the hinge portion 203 of the print wiring board 214.

Further, in the mobile phone 200, the CPU 200A (see FIG. 12) may record data such as date and time when the cell phone 200 got wet, in the memory 200B (see FIG. 12).

In this case, the data such as date and time when the cell phone 200 got wet is read from the memory 200B to check whether the cell phone 200 got wet, and what date and time it happened, for example. Therefore, when a failure occurs in the mobile phone 200, it is possible to judge: whether or not the failure caused by adhesion of water; or the failure is caused by user's mishandling or caused by a manufacturer by having the cell phone 200 got wet before its sale.

Patterns of combination in the present invention may be a pattern of the above exemplary embodiments or combining two or more examples among the above exemplary embodiments.

The flow of the processing program described in the above exemplary embodiments (see FIG. 16) is merely an example and may be appropriately changed within the scope of the present invention.

Further, it is noted that the inventor's intent is to retain all equivalents of the claimed invention even if the claims are amended during prosecution.

What is claimed is:

1. A moisture detection label, comprising:
   a base material;
   at least a pair of detection terminals provided on the base material; and
   a pattern of water-dispersible and conductive paint provided on the front surface of the base material and formed between the detection terminals,
   wherein the base material has grooves across the detection terminals,
   wherein the water-dispersible and conductive paint is a conductive electrodeposition paint comprising an ionic substance with ink,
   wherein when moisture does not adhere to the pattern, there is no electrical connection between the detection terminals, and
   wherein when moisture adheres to the pattern, the pattern swells or disperses to form an electrical connection between the detection terminals.

2. The moisture detection label according to claim 1, wherein the pattern swells by absorbing moisture and is dispersed over the front surface of the base material toward the detection terminals.

3. The moisture detection label according to claim 1, wherein two or more of the patterns are provided between the detection terminals.

4. The moisture detection label according to claim 3, wherein the two or more of the patterns are arranged in a lattice pattern.

5. The moisture detection label according to claim 1, wherein each of the detection terminals is provided on an outer periphery of the base material in a manner that the detection terminals are opposed to each other.

6. The moisture detection label according to claim 1, wherein the base material is formed into a sheet-like shape, and the detection terminals are provided from the front surface to a rear surface of the base material.

7. A moisture detection device, comprising:
a moisture detection label that has at least a pair of detection terminals and a pattern,
wherein the detection terminals are provided on a base material, the pattern comprises water-dispersible and conductive paint and is provided on the front surface of the base material and formed between the detection terminals, and the base material has grooves across the detection terminals; and
a detector that detects an electrical connection state between the detection terminals of the moisture detection label,
wherein when moisture does not adhere to the pattern, there is no electrical connection between the detection terminals, and
wherein when moisture adheres to the pattern, the pattern swells or disperses to form an electrical connection between the detection terminals.

8. The moisture detection device according to claim 7, wherein the detector includes a Wheatstone bridge, and the Wheatstone bridge has a nonequilibrium when the detection terminals are electrically connected.

9. The moisture detection device according to claim 8, wherein, the Wheatstone bridge includes resistors connected in series to one of the detection terminals of the moisture detection label, and
wherein, each resistor has a resistance value different from one another.

10. The moisture detection device according to claim 7, wherein the pattern swells by absorbing moisture and is dispersed over the surface of the base material toward the detection terminals.

11. A moisture detection method comprising:
providing a moisture detection label that includes at least a pair of detection terminals and a pattern, the detection terminals being provided on a base material, the pattern containing water-dispersible and conductive paint and being formed between the detection terminals, whereby the paint swells by absorbing moisture to thereby disperse toward the detection terminals; and
detecting an electrical connection state caused between detection terminals through the dispersed paint, and
wherein the water-dispersible and conductive paint is a conductive electrodeposition paint comprising an ionic substance with ink,
wherein when moisture does not adhere to the pattern, there is no electrical connection between the detection terminals, and
wherein when moisture adheres to the pattern, the pattern swells or disperses to form an electrical connection between the detection terminals.

12. The moisture detection method according to claim 11, wherein an electrical connection state between the detection terminals is detected in a Wheatstone bridge, and the Wheatstone bridge has a nonequilibrium state when the detection terminals are electrically connected.

13. The moisture detection method according to claim 12, wherein, in the Wheatstone bridge, resistors connected in series to one of the detection terminals of the moisture detection label each has a resistance value different from one another.

14. An electronics device, comprising:
a device main body having power source;
a moisture detection label that is provided on the device main body, and has at least a pair of detection terminals and a pattern,
wherein the detection terminals are provided on a base material, the pattern comprises a water-dispersible and conductive paint and is provided on the surface of the base material and is formed between the detection terminals, and the base material has grooves across the detection terminals; and
detector that is provided on the device main body and detects an electrical connection state between the detection terminals of the moisture detection label, and
wherein the water-dispersible and conductive paint is a conductive electrodeposition paint comprising an ionic substance with ink,
wherein when moisture does not adhere to the pattern, there is no electrical connection between the detection terminals, and
wherein when moisture adheres to the pattern, the pattern swells or disperses to form an electrical connection between the detection terminals.

15. The electronics device according to claim 14, further comprising:
power shutoff means for shutting off power based on the electrical connection state detected by the detector.

16. The electronics device, according to claim 15, further comprising:
control means for causing storing means to store data before the power shutoff means shuts off power.

17. The electronics device according to claim 14, further comprising:
warning means for warning of adhesion of water based on the electrical connection state detected by the detector.

18. A power shutoff method used in a moisture detection label that includes at least a pair of detection terminals and a pattern, the detection terminals being provided on a base material, the pattern containing water-dispersible and conductive paint and being formed between the detection terminals, the power shutoff method comprising:
detecting an electrical connection state between the detection terminals; and
shutting off power in a case where it is detected that the detection terminals are electrically connected, and
wherein the water-dispersible and conductive paint is a conductive electrodeposition paint comprising an ionic substance with ink,
wherein when moisture does not adhere to the pattern, there is no electrical connection between the detection terminals, and
wherein when moisture adheres to the pattern, the pattern swells or disperses to form an electrical connection between the detection terminals.

19. The power shutoff method according to claim 18, further comprising:
causing storing means to store data before shutting off power, in a case where it is detected that the detection terminals are electrically connected.

20. The power shutoff method according to claim 18, further comprising:

causing warning means to warn of adhesion of water before shutting off power, in a case where it is detected that the detection terminals are electrically connected.

21. The moisture detection label according to claim 1, wherein the base material has an insulated front surface.

22. The moisture detection device according to claim 7, wherein the base material has an insulated front surface.

23. The electronic device according to claim 14, wherein the base material has an insulated front surface.

24. The moisture detection label according to claim 1, wherein the pattern is configured to disperse upon contact with water.

25. The moisture detection device according to claim 7, wherein the pattern is configured to disperse upon contact with water.

26. The electronic device according to claim 14, wherein the pattern is configured to disperse upon contact with water.

27. The power shutoff method according to claim 18, wherein the pattern is configured to disperse upon contact with water.

28. The moisture detection label according to claim 1, further comprising a processor for determining when there is an electrical connection resulting from the swelling or dispersion of the pattern.

29. The moisture detection device according to claim 7, further comprising a processor for determining when there is an electrical connection resulting from the swelling or dispersion of the pattern.

30. The electronic device according to claim 14, further comprising a processor for determining when there is an electrical connection resulting from the swelling or dispersion of the pattern.

* * * * *

UNITED STATES PATENT AND TRADEMARK OFFICE
CERTIFICATE OF CORRECTION

Page 1 of 1

PATENT NO. : 8,441,362 B2
APPLICATION NO. : 13/443432
DATED : May 14, 2013
INVENTOR(S) : Shinji Oguri It is certified that error appears in the above-identified patent and that said Letters Patent is hereby corrected as shown below:

In the Specification

Column 2, line 34: Delete "abase" and insert -- a base --.

Column 4, Line 8: Before "includes:" insert -- 10 --.

Column 4, Line 14-21: Delete "The thin-plate like……………..non-transparent material." and insert the same on Col. 4, Line 15, as a new Paragraph.

Column 5, Line 29: Delete "101R" and insert -- 101B --.

Column 8, Line 42-43: Delete "The battery 111…………………..electronics device 200." and insert the same on Col. 8, Line 41 after "115c." as a continuation of the same Paragraph.

Signed and Sealed this
Eleventh Day of November, 2014

Michelle K. Lee
*Deputy Director of the United States Patent and Trademark Office*